United States Patent
Biemans et al.

(10) Patent No.: US 8,516,714 B2
(45) Date of Patent: Aug. 27, 2013

(54) METHOD FOR LYOPHILISING PARTICLES HAVING A PHARMACEUTICAL COMPOUND CONTAINED THEREIN AND A PHARMACEUTICAL PACK CONTAINING SUCH PARTICLES

(75) Inventors: Rogier Biemans, Boxmeer (NL); Monique Kirkels, Boxmeer (NL); Hans Almer Middelbeek, Boxmeer (NL)

(73) Assignee: Intervet International B.V., Boxmeer (NL)

( * ) Notice: Subject to any disclaimer, the term of this patent is extended or adjusted under 35 U.S.C. 154(b) by 317 days.

(21) Appl. No.: 12/863,537

(22) PCT Filed: Jan. 20, 2009

(86) PCT No.: PCT/EP2009/050584
§ 371 (c)(1),
(2), (4) Date: Oct. 5, 2010

(87) PCT Pub. No.: WO2009/092703
PCT Pub. Date: Jul. 30, 2009

(65) Prior Publication Data
US 2011/0016740 A1    Jan. 27, 2011

Related U.S. Application Data

(60) Provisional application No. 61/022,387, filed on Jan. 21, 2008.

(30) Foreign Application Priority Data

Jan. 21, 2008   (EP) .................................... 08150461

(51) Int. Cl.
*F26B 5/06*   (2006.01)

(52) U.S. Cl.
USPC .............. 34/284; 62/50.7; 206/528; 264/299; 425/357

(58) Field of Classification Search
USPC ............... 34/284, 287, 90, 92; 62/50.1, 50.7, 62/533; 206/528, 438; 264/299; 425/357
See application file for complete search history.

(56) References Cited

U.S. PATENT DOCUMENTS 2,441,730 A * 5/1948 Strumia ......................... 34/295
(Continued)

FOREIGN PATENT DOCUMENTS

EP    0 308 238 A1   3/1989
(Continued)

OTHER PUBLICATIONS

Chueshov et al., "Manufacturing Technologies of Medicines", Textbook for High School Students, Harkov, 2002, pp. 501-512, vol. 1 (Translation Attached).
(Continued)

*Primary Examiner* — Steve M Gravini
(74) *Attorney, Agent, or Firm* — David J. Kerwick

(57) ABSTRACT

The present invention pertains to a method for lyophilizing particles comprising frozen liquid having a pharmaceutical compound contained therein, comprising providing a heat conducting container having a bottom and side walls, filling the container with a bed of the particles, the bed comprising multiple layers of the particles and having an aspect ratio of not less than 1, providing a heat source above a top layer of the particles, the heat source having a surface directed to a top layer of the bed, which surface has an emissivity coefficient of at least 0.4, subjecting the particles filled in the container to a reduced pressure, heating at least the bottom of the container and the said surface to provide heat to the particles to support sublimation of the frozen liquid at the reduced pressure, and after the frozen liquid is sublimated, stopping the provision of heat to the particles. The invention also pertains to a pharmaceutical pack comprising a container having contained therein at least one particle obtained via this method.

11 Claims, 1 Drawing Sheet

(56) References Cited

U.S. PATENT DOCUMENTS

Figure 1:
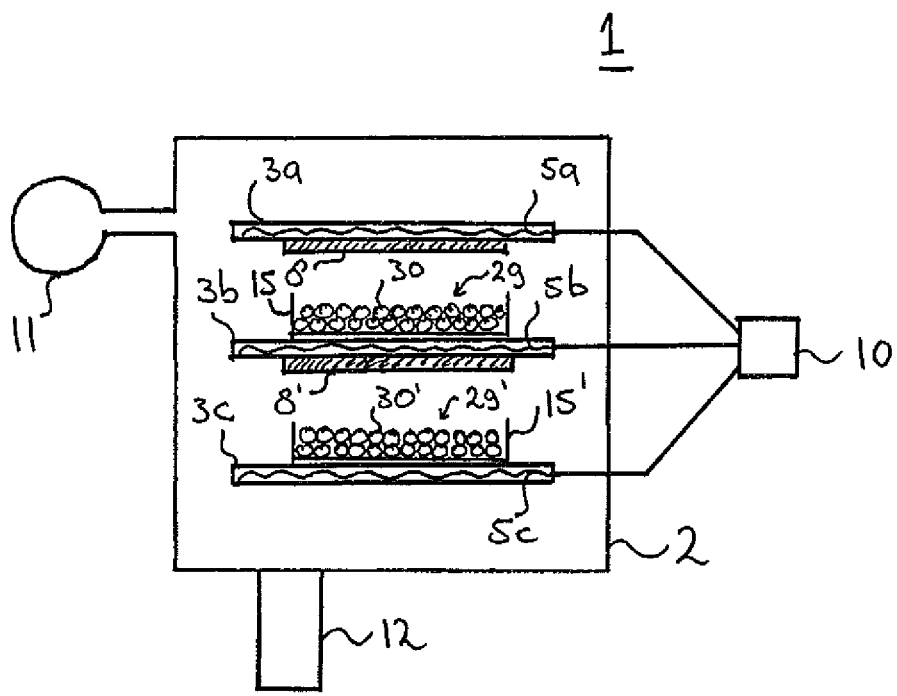

| | | | |
|---|---|---|---|
| 3,313,032 A * | 4/1967 | Malecki | 34/288 |
| 3,431,655 A * | 3/1969 | Ganiaris et al. | 34/287 |
| 3,462,849 A * | 8/1969 | Gidlow | 34/299 |
| 3,486,907 A | 12/1969 | Hair et al. | |
| 3,545,097 A | 12/1970 | Waltrich | |
| 3,731,392 A * | 5/1973 | Gottfried | 34/291 |
| 3,932,943 A | 1/1976 | Briggs et al. | |
| RE28,965 E * | 9/1976 | Hamilton | 34/92 |
| 4,096,283 A * | 6/1978 | Rahman | 426/242 |
| 5,230,162 A * | 7/1993 | Oyler, Jr. | 34/292 |
| 6,584,782 B2 * | 7/2003 | Leuenberger et al. | 62/64 |
| 7,836,606 B2 * | 11/2010 | Gehrmann et al. | 34/284 |
| 2003/0180755 A1 * | 9/2003 | Hwang et al. | 435/6 |
| 2005/0019393 A1 * | 1/2005 | Augsburger et al. | 424/464 |
| 2005/0266021 A1 | 12/2005 | Maa et al. | |
| 2008/0060213 A1 * | 3/2008 | Gehrmann et al. | 34/284 |
| 2011/0016740 A1 * | 1/2011 | Middelbeek et al. | 34/284 |
| 2012/0048764 A1 * | 3/2012 | Middelbeek et al. | 206/438 |
| 2012/0049412 A1 * | 3/2012 | Middlebeek et al. | 264/299 |

FOREIGN PATENT DOCUMENTS

| | | |
|---|---|---|
| EP | 0 695 171 B1 | 12/1996 |
| EP | 0 799 613 B1 | 7/2001 |
| JP | 01176221 A * | 7/1989 |
| JP | 06166576 A * | 6/1994 |
| JP | 06172177 A * | 6/1994 |
| JP | H06257941 A | 9/1994 |
| JP | 09248177 A1 | 9/1997 |
| JP | 2001012856 A | 1/2001 |
| JP | 2006177640 A | 7/2006 |
| WO | 2006/008006 A1 | 1/2006 |

OTHER PUBLICATIONS

Jafar et al,, "Analysis of Heat and Mass Transfer in Freeze Drying", Drying Technology, 2003, pp. 249-263, vol. 2, No. 2.

International Search Report for corresponding PCT/EP2009/050584, mailed Apr. 20, 2009.

* cited by examiner

METHOD FOR LYOPHILISING PARTICLES HAVING A PHARMACEUTICAL COMPOUND CONTAINED THEREIN AND A PHARMACEUTICAL PACK CONTAINING SUCH PARTICLES

The present invention pertains to a method for lyophilising particles comprising frozen liquid having a pharmaceutical compound contained therein. The invention also pertains to a pharmaceutical pack comprising a container having contained therein at least one particle obtained by such a method.

From EP 799613 such a method and pack are known. In particular a method is described for obtaining frozen particles with a typical size of about 0.2 mm to about 10 mm, which particles contain as a pharmaceutical compound one or more antigens originating from micro-organisms, in particular the micro-organisms as a whole, either live or killed, or sub-units derived from these micro-organisms. These particles can be freeze-dried ("lyophilised") to obtain particles that can be stored for long times at temperatures above 0° C. without any significant loss in efficacy. Disadvantage of the known method however is that freeze-drying of a batch of particles, often results in a relatively large spread in effective content of the particles, even if the frozen particles, directly before the drying step, are very homogenous with respect to effective content. Next to this, agglomeration of particles may take place during the drying step.

From WO 2006/008006 also a method of freeze-drying particles containing a pharmaceutical compound is known. In order to achieve homogenous drying conditions and prevent particles from agglomeration, continuous vibration of the containers that hold the particles to be dried is recommended. However, since the mechanical stability of lyophilised particles is typically not very high, it is proposed to vibrate the particle containers at regular intervals. An important disadvantage of this method is that particles themselves tend to be broken and lots of fine particulate material is provided. This fine particulate material is difficult to handle. Moreover, to be able and vibrate the containers that hold the particles during drying, the freeze-dry equipment as a whole is vibrated. For this reason, standard equipment cannot be used which makes the method economically very unattractive.

It is an object of the present invention to overcome or at least mitigate the disadvantages of the prior art method. To this end, a method has been devised comprising providing a heat conducting container having a bottom and side walls, filling the container with a bed of the particles, the bed comprising multiple layers of the particles and having an aspect ratio of not less than 1, providing a heat source above a top layer of the particles, the heat source having a surface directed to a top layer of the bed, which surface has an emissivity coefficient of at least 0.4, subjecting the particles filled in the container to a reduced pressure, heating at least the bottom of the container and the said surface to provide heat to the particles to support sublimation of the frozen liquid at the reduced pressure, and after the frozen liquid is sublimated, stopping the provision of heat to the particles.

In the present method, frozen particles are being freeze-dried. The term "frozen particle" in this sense means that a constituent of the particle that is liquid at room temperature is brought in a non-liquid state and can thus be regarded as frozen liquid. Such state may be a crystalline one, an amorphous one or a mixture of both. The frozen particles are brought into a heat conducting container, e.g. a type of container not having a lid but being open at the top. The particles form a bed in the container, the bed comprising multiple layers of particles, typically (but not necessarily) 2 to 10 layers. An aspect ratio of the bed, i.e. the ratio of a width of the bed and the height of the bed should not be less than one. This appears to improve the drying performance (especially efficiency) of the present method. The particles are then subjected to a reduced pressure whereafter heat is supplied to the particles by heating at least the bottom of the container (which container transfers heat to the particles at least via conduction) and a surface that is provided above the container (which surface provides heat to the particles via irradiation). This surface has an emissivity coefficient of at least 0.4, preferably even 0.7 or higher. The emissivity coefficient (usually denoted as $\epsilon$) in this respect is the ratio of energy radiated by the surface to energy radiated by a true black body of the same temperature. It is a measure of the ability to absorb and radiate energy. A true black body would have an $\epsilon=1$ while any real surface or object would have $\epsilon<1$. Emissivity is a numerical value and does not have units. By having an emissivity coefficient of at least 0.4, the heated surface radiates relatively high quantities of heat to the particles. By providing sufficient heat, the frozen liquid keeps sublimating at the reduced pressure (as is commonly known in the art) and the particles are dried (i.e. they lose a substantial part of their frozen liquid). Typically a residual moisture content of less then 5%, preferably less than 3% and even more preferably less than 1.5% can be obtained. However, a higher content may be satisfactory depending on the pharmaceutical compound and the intended use of the particles. As soon as an adequate level of residual moisture content is reached, the process can be regarded as finished. The provision of heat to the particles can then be stopped to prevent temperature rise of the particles. At this stage the frozen liquid is said to have been sublimated in the sense of the present invention, although residual material of the frozen liquid might still be contained in the particles. The present method appears to be efficient, simple and economically attractive way, and still provides very homogenous drying properties. Freeze-dried particles can be obtained with no, or at least relatively few, agglomerates being formed during the drying process.

The present invention can be advantageously used with various pharmaceutical compounds. Such compounds may e.g. be a micro-organism (e.g. bacterium, virus, rickettsia, protozoan etc) or sub-unit derived therefrom, either obtained from nature itself or made via recombinant techniques, but the compound may also be a drug, e.g. a synthesized drug. Examples of drugs that have been formulated in frozen particles are known i.a. from EP 0 695 171 and U.S. Pat. No. 3,932,943. In each case, the obtainable advantages, which in particular pertain to the physical features of the drying process, are important for obtaining high quality end products.

It is noted that the application of radiation as such in a freeze-dry process is known in the art. For example, in Drying Technology, Vol. 21, No. 2, pp. 249-263, 2003, it is described that radiation can be used to sufficiently heat a compound to be dried. However, from this reference it becomes clear that radiation is a mere substitute for conduction and provides the same drying results. Therefore it came as a surprise to applicant that the combined use of conduction (i.e. providing heat to the particles via contact with the heated bottom of the container) and radiation under the circumstances as defined in claim 1 provided a substantially different result for drying particulate material, viz. less or no agglomerates appeared and a homogenous effective content could be provided.

In an embodiment the aspect ratio of the bed is not less than 5, in particular not less than 10. It appears that providing these preferred ratios provides the possibility of obtaining a higher throughput with the current method without loss of drying quality.

In another embodiment of the present method, in which embodiment the bottom and side walls of the container each have a surface directed to the bed of particles, each of these surfaces has an emissivity coefficient of at least 0.4, in particular at least 0.7. This way, the container cannot only provide sufficient quantities of heat to the particles via conduction but also via irradiation. It appears that by using a container of this kind, very good drying results can be obtained. Preferably, the emissivity coefficient of the heat source has the same or a higher value than the emissivity coefficient of the container bottom and side walls.

In an embodiment wherein the bottom of the container is heated by using a first heating plate, as the heat source above the top layer of the particles a second heating plate is used. This leads to a simple construction of the freeze-dry equipment without having to lose any advantages of the present invention. Moreover a plate has the advantage, in particular when heated evenly, of being capable to very homogenously radiate heat to its surroundings. When using e.g. heating tape or coil as irradiating heating element, it would be less easy to provide a source of radiation that radiates approximately the same amount of radiation at each site of the particle bed.

In a further embodiment wherein the second heating plate has in essence the same constitution as the first heating plate, the side of the second plate directed to the top layer is provided with a material that has the emissivity coefficient of at least 0.4. This way, the advantages of the present invention can be obtained using standard freeze-dry equipment. In an embodiment the lower side of the second heating plate is provided with a coating providing the said emissivity coefficient. Alternatively the lower side of the second heating plate is provided with an additional plate, which plate has the said emissivity coefficient. It is self-evident that the coating or additional plate should be in good thermal contact with the second heat plate. For a coating this may be inherent. In case of an additional plate one should make sure that there is a good thermal contact, e.g. by using any art-known technique as using a thermal conductive glue, using a very tight mechanical means of adhering the surfaces such as welding, or any other technique.

In case an additional plate is being used, it is preferred that this plate is made of a fluoropolymer, in particular polytetrafluoroethylene (PTFE). By using a fluoropolymer to constitute the plate, a plate can be provided that is relatively cheap, but still has very god cleanability properties, which is an important advantage especially in case pharmaceutical containing particles are freeze-dried.

In an embodiment the heat is provided to the particles by heating the first heating plate to the same temperature as the second heating plate. This simplifies the control of the freeze-drying process. Moreover, the second heating plate can be used as a heat source to heat the bottom of a second container to the same temperature as the bottom of the first container.

It is noted that the invention also pertains to a pharmaceutical pack comprising a container, e.g. a vial, tube, syringe, blister etc., having contained therein at least one particle obtained by a method according to the present invention. In particular, the present invention pertains to a container having contained therein one or more freeze-dried particles containing antigen (i.a. a substance that initiates and mediates the formation of the corresponding immune body, usually a micro-organism and/or a sub-unit derivable therefrom, either obtained via essentially biological techniques or via the use of recombinant techniques), which can be reconstituted as part of a vaccine for oral or parenteral administration.

The invention will now be further explained using the following examples and figures.

Example 1 describes various methods to obtain frozen particles containing one or more pharmaceuticals.

Example 2 in conjunction with FIGS. 1 (lyophiliser, schematically depicted) and 2 (container, schematically depicted) describes a freeze-dry apparatus for use in the present invention.

Example 3 describes a method suitable for freeze-drying frozen particles and the results obtainable.

Example 4 describes methods for measuring emissivity coefficients for various surfaces.

EXAMPLE 1

It is commonly known in the art how to produce frozen particles containing a pharmaceutical content. This is described i.a. in EP 799613 (assigned to AKZO Nobel NV), JP 09248177 (assigned to Snow Brand Milk Corp) and WO 2006/008006 (assigned to Bayer Technology Services GmbH). It is also known from these references that such particles can be lyophilized to obtain "dry" and stable particles. In the latter reference numerous alternative methods for producing frozen particles are mentioned. These are summed up, beginning at page 4, line 23 ("There are many methods known to those skilled in the art . . . ") and ending on page 8, line 13 (" . . . The process is suitable for frozen granules or pellets."). Next to these known methods numerous other methods are known to obtain frozen pellets with a pharmaceutical compound contained therein, either leading to spherical or otherwise shaped particles. In the present case, we have used a technique as known from JP 09248177 to obtain frozen spherical pellets with an average diameter of approximately 6 mm. A size between 1 and 15 mm is most commonly used, in particular a size between 2 and 10 mm.

It is noted that the liquid can in principal be any liquid. In many cases, the main constituent of the liquid is water. Generally, the liquid is a carrier for the pharmaceutical compound in the production process of the compound. However, it can also be added as a medium to the compound for obtaining a constitution that can be easily processed to obtain frozen particles. In case the pharmaceutical compound is a microorganism or subunit thereof, the liquid often consists substantially of fermentation broth or a fraction thereof, such as supernatant (e.g. in case the compound arises from an industrial fermentor) or allantois fluid (e.g. in case the compound arises from fermentation in eggs), optionally comprising additional fluids and/or other constituents for providing e.g. good processing or desired ultimate product properties such as storage stability.

EXAMPLE 2

In FIG. 1 a lyophiliser (freeze-dry apparatus) is schematically depicted. Such a lyophiliser could for example be the Christ Epsilon 2-12D as available from Salm en Kipp, Breukelen, The Netherlands. The lyophiliser 1 comprises a housing 2 and multiple shelves 3. The Epsilon 2-12D comprises 4+1 shelves, for matters of convenience three of these shelves (viz. shelves 3a, 3b and 3c) are shown in FIG. 1. Each of these shelves is provided with a heating element 5 (referred to with numerals 5a, 5b and 5c respectively) for even heating of the shelves 3. The heating is controlled by making use of processing unit 10. The housing is connected to a pump unit 11 for providing adequate low pressure within the housing 2. The interior of the housing can be cooled to a temperature as low as −60° C. by using cooling unit 12, in particular containing a condensor. Shelves 3a and 3b are provided with black PTFE plates 8 and 8' fixed to their bottom. The emissivity coefficient of these plates is 0.78. By intimate contact between these black plates and the shelves, these plates can be warmed virtually to the same temperature as the shelves themselves. This way, the plates 8 can be regarded as heat source in addition to the shelves 3 themselves.

Figure 2:
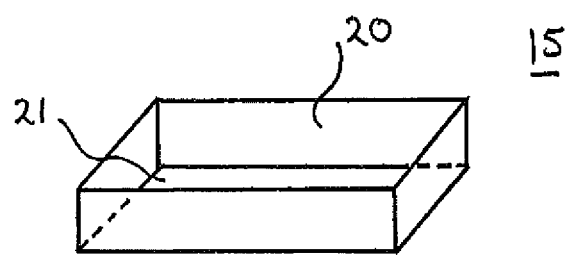

Placed on the shelves are container 15 and 15'. These containers are made of a heat conducting material, in this case carbon black filled polyethyleneterephtalate. The containers are in a heat conducting contact with the shelves on which they rest. The containers are filled with frozen particles 30 which thus form a bed 29 of packed particles in each container. By heating the shelves, the particles may receive heat via the heated bottom and side walls of the containers and by irradiation from the heated plates 8 and 8' respectively. FIG. 2 gives a view of the containers 15 themselves. Each container comprises a bottom 21 and sidewalls 20. Typically, the container has a width and length of about 20 to 30 cm and a height of about 4 cm. The height of the packed bed after filling the container is typically 1.5 to 3 cm. This leads to typical values for an aspect ratio of the bed of between 20/3≈7 to about 30/1.5=20.

In this example, the heat source with the high emissivity coefficient is the PTFE plate 8 (and 8'). Alternatively, the shelves could have been provided with a black paint to provide a emissivity coefficient of 0.4 or higher. Another possibility would have been to chemically (e.g. by etching) and/or mechanically (e.g. by sanding or sandblasting) change the surface of the shelves 3 (which in case of the Epsilon 2-12D are made of stainless steel) to provide an adequate emissivity coefficient.

In an alternative lyophiliser the containers 15 are heated via radiation. Although conduction is preferred because of convenience and speed, heating the containers via a radiation heater element beneath each of the containers is also a usable option. The same heater could then be used for providing heat to a top layer of a packed bed of frozen particles lying beneath the heater element.

The container can be made of various heat conducting materials such as plastic, glass, metal or even composite materials. It is preferred that the container is open at the top such that sublimated gas can easily escape from the packed bed. However, it has been described that sublimated carrier liquid can also be successfully removed from a container when this container is essentially closed and only contains holes in the lid to release the sublimated material. Advantage of a container with a lid is that the lid itself could serve as a radiating heat source.

EXAMPLE 3

For obtaining lyophilised particles we used the method as mentioned in example 1 and the Christ Epsilon 2-12D lyophiliser, having the heat sources with a high emissivity coefficient surface as described in example 2. To obtain the frozen particles, in this example live virus was harvested from eggs. In some cases (viz. for IB and ND virus, see Table 2) the allantois fluid containing the virus, mixed with stabilizer, was frozen into spherical pellets, in other cases (viz. for Gumboro type virus, see Table 2) homogenized chicken embryo fluid, after it was filtered and a stabilizer had been added, was frozen into spherical pellets. The frozen particles (having a temperature of about minus 60° C.) were put in the containers (as described in example 2) to obtain a packed bed with an aspect ratio of about 15. The containers were then put in the lyophiliser which had already been brought to a temperature of about −35° C. The lyophiliser was subjected to the following freeze-drye cycle (Table 1).

TABLE 1

| Phase | Time [h:m] | Temp [° C.] | Vacuum [mbar] |
|---|---|---|---|
| Freezing | 00:30 | −35 | 1000 |
| Preparation | 00:20 | −35 | 1000 |
| Initial sublimation | 00:10 | −35 | 0.370 |
| Sublimation 1 | 03:00 | 40 | 0.370 |
| Sublimation 2 | 16:00 | 40 | 0.370 |
| Closing step | 00:01 | 4 | 0.021 |

As can be seen in Table 1, after loading the shelves with the filled containers the shelves are firstly kept at a temperature of −35° C. for 30 minutes (the "Freezing" phase). Herewith the particles are brought to a temperature of −35° C. The pressure is kept atmospheric. Then, the temperature of the shelves is stabilized at −35° C. during 20 minutes, pressure is still atmospheric ("Preparation"). Then, the pressure is lowered to 0.370 mbar in a period of ten minutes, the temperature of the shelves is kept at −35° C. ("Initial sublimation"). Under these conditions, the frozen liquid already sublimates and heat is supplied to the particles via the heat sources. However, the speed of sublimation under these conditions is relatively low. To increase the speed of sublimation, the shelves are brought to a temperature of 40° C. in a period of 3 hours ("Sublimation 1"), and kept at that temperature for 16 hours ("Sublimation 2"). The pressure is kept at the low value of 0.370 mbar. Thereafter, the pressure is further reduced to 0.021 mbar whilst the temperature of the shelves is brought to 4° C. This latter step takes 1 minute ("Closing step"). After that, the sublimation process is completed and about 98% of the frozen liquid has left the particles. Then, dried nitrogen gas with a temperature of about 20° C. is led into the lyophiliser until the pressure is about atmospheric. This takes about 2 minutes. Then the door can be opened to take out the dried particles. When using the present method, it can be seen that a homogenous lyophilising result can be obtained, visible as a homogenous bed of lyophilized particles. After opening the lyophiliser, the particles are not subjected to a humid environment to try and prevent condensation of water on the particles. In particular, the particles are filled in small containers in a closet with an atmosphere of dried air. After filling the containers, they are closed and stored in a cool place (4-8° C.) until further use.

This way, lyophilized spheres were obtained with an average diameter of approximately 6 mm and having contained therein a pharmaceutical compound as shown in Table 2. The overall composition of these freeze-dried particles, in particular the compounds that form the carrier material for the pharmaceutical ingredient, is in essence the same as the freeze-dried pellets of corresponding vaccines obtainable from Intervet Nederland b.v., Boxmeer, The Netherlands (corresponding product names are indicated in Table 2 as well).

TABLE 2

| Pharmaceutical component | Corresponding Intervet product | Dose of active component per particle [$\log^{10}$ EID$_{50}$] |
|---|---|---|
| Live Infectious Bronchitis virus, strain 4-91 | Nobilis IB 4/91 | 6.6 |
| Live infectious bronchitis virus, serotype Massachusetts, Ma5 | Nobilis IB Ma5 | 6.5 |
| Live infectious bronchitis virus, serotype Massachusetts, H120 | Nobilis IB H120 | 6.0 |
| Live Newcastle Disease virus | Nobilis ND Clone 30 | 8.5 |

TABLE 2-continued

| Pharmaceutical component | Corresponding Intervet product | Dose of active component per particle [$\log^{10}$ EID$_{50}$] |
|---|---|---|
| Live Newcastle Disease virus | Nobilis ND LaSota | 9.0 |
| Live infectious bursal disease virus | Nobilis Gumboro 228E | 4.2 |
| Live infectious bursal disease virus | Nobilis Gumboro D78 | 6.7 |

Although the method according to the present invention has been specifically exemplified by using live viruses as the pharmaceutical compound contained in the freeze-dried particles, it may be clear to the skilled artisan that the advantages of the present invention, in particular the homogenous drying result, can be harvested also when another type of pharmaceutical compound is contained in the particles, such as another micro-organism, an active molecule, a subunit of a micro-organism, or any other pharmaceutical compound.

The lyophilized particles are used to provide a pharmaceutical pack. This pack consists of a container (such as a glass or plastic vial) containing one or more of the lyophilized particles and optionally other constituents. The pharmaceutical compound in the lyophilized particle can be administered to a patient e.g. by direct oral take up of the particle itself, but it is also possible to reconstitute the particle for example with a liquid, such that a composition is obtained that is suitable for drinking or parenteral administration (such as subcutaneous, intramuscular, submucosal and intradermal administration) via injection of the fluid.

EXAMPLE 4

Emissivity in the sense of the present invention is the mean emissivity as established at four different temperatures of the surface, viz. 55, 60, 65 and 70° C. The emissivity can be measured by using dedicated emissivity measurement equipment as commercially available such as the Model 205WB of Advanced Fuel Research Inc., East Hartford, Conn. USA. Such equipment however is very expensive. Alternatively, as commonly known, a very simple way of measuring the emissivity is to heat the surface and a surface with a known emissivity to the same temperature as determined by a thermocouple. Then read the temperature of the two surfaces with a standard infrared pyrometer. The difference in the two infrared temperature measurements is due to the difference in the emissivities of the surfaces (see also Applied Optics, Vol. 13, No 9, September 1974). We chose this method to obtain the emissivity coefficient of various types of surfaces for use in our experiments. Obtainable results are given below in Table 2.

TABLE 2

Emissivity coefficients of various surfaces

| Surface | Emissivity coefficient [-] |
|---|---|
| Ice | 0.96 |
| Glass | 0.92 |
| Carbon black paint | 0.88 |
| Stainless steel | 0.22 |
| Polished stainless steel | 0.11 |
| Etched stainless steel | 0.25 |
| Sandblasted stainless steel | 0.40 |
| Sandblasted and etched stainless steel | 0.49 |
| PTFE (smooth surface) | 0.78 |

It appears that the advantages of the present method can be obtained when using a surface having an emissivity coefficient of 0.4 or higher. Indeed, ice is not a very practical option since this material sublimates or even melts at the temperatures normally used for the plates in a freeze-dryer.

What is claimed:

1. A method for lyophilising particles comprising frozen liquid having a pharmaceutical compound contained therein, comprising:
    providing a heat conducting container having a bottom and side walls,
    filling the container with a bed of the particles, the bed comprising multiple layers of the particles and having an aspect ratio of not less than 1,
    providing a heat source above a top layer of the particles, the heat source having a surface directed to a top layer of the bed, which surface has an emissivity coefficient of at least 0.4,
    subjecting the particles filled in the container to a reduced pressure,
    heating at least the bottom of the container and the said surface to provide heat to the particles to support sublimation of the frozen liquid at the reduced pressure,
    after the frozen liquid is sublimated, stopping the provision of heat to the particles.

2. A method according to claim 1, characterised in that a heat source is provided of which the surface has an emissivity coefficient of at least 0.7.

3. A method according to claim 1, wherein the aspect ratio of the bed is not less than 5, in particular not less than 10.

4. A method according to claim 1, wherein the bottom and side walls of the container each have a surface directed to the bed of particles, characterised in that each of these surfaces has an emissivity coefficient of at least 0.4, in particular at least 0.7.

5. A method according to claim 1, wherein the bottom of the container is heated by using a first heating plate, characterised in that for providing the heat source above the top layer of the particles a second heating plate is used.

6. A method according to claim 5, wherein the second heating plate has in essence the same constitution as the first heating plate, characterised in that the side of the second plate directed to the top layer is provided with a material that has the emissivity coefficient of at least 0.4.

7. A method according to claim 6, characterised in that the lower side of the second heating plate is provided with a coating providing the said emissivity coefficient.

8. A method according to claim 6, characterised in that the lower side of the second heating plate is provided with an additional plate, which plate has the said emissivity coefficient.

9. A method according to claim 8, characterised in that the additional plate is made of a fluoropolymer, in particular polytetrafluoroethylene.

10. A method according to claim 1, characterised in that for the provision of heat to the particles the first heating plate is heated to the same temperature as the second heating plate.

11. A pharmaceutical pack comprising a container having contained therein at least one particle obtained by a method according to claim 1.

* * * * *